US008118864B1

(12) United States Patent
Escano et al.

(10) Patent No.: US 8,118,864 B1
(45) Date of Patent: Feb. 21, 2012

(54) DRUG DELIVERY ENDOVASCULAR GRAFT

(75) Inventors: Arnold M. Escano, Santa Clara, CA (US); Joanne L. Parker, Fremont, CA (US); Rodney Reinhardt, Flintstone, GA (US)

(73) Assignee: Endovascular Technologies, Inc., Santa Clara, CA (US)

( * ) Notice: Subject to any disclaimer, the term of this patent is extended or adjusted under 35 U.S.C. 154(b) by 1919 days.

(21) Appl. No.: 10/854,014

(22) Filed: May 25, 2004

(51) Int. Cl.
*A61F 2/82* (2006.01)

(52) U.S. Cl. .................................................... 623/1.42

(58) Field of Classification Search ................. 623/1.35, 623/1.42, 1.43, 1.45

See application file for complete search history.

(56) References Cited

U.S. PATENT DOCUMENTS 5,197,977 A 3/1993 Hoffman, Jr. et al.
5,383,928 A 1/1995 Scott et al.
5,545,208 A * 8/1996 Wolff et al. .................. 623/1.22
5,591,227 A 1/1997 Dinh et al.
5,599,352 A 2/1997 Dinh et al.
5,697,967 A 12/1997 Dinh et al.
5,843,118 A * 12/1998 Sepetka et al. ............... 623/1.15
6,039,758 A * 3/2000 Quiachon et al. ............. 128/898
6,071,305 A 6/2000 Brown et al.
6,174,330 B1 * 1/2001 Stinson ......................... 623/1.34
6,221,102 B1 * 4/2001 Baker et al. ................... 623/1.36
6,235,050 B1 * 5/2001 Quiachon et al. ............ 623/1.11
6,287,330 B1 * 9/2001 Johansson et al. ........... 623/1.13
6,340,367 B1 * 1/2002 Stinson et al. ............... 623/1.34
6,355,063 B1 3/2002 Calcote
6,458,152 B1 * 10/2002 Khosravi et al. ............. 623/1.13
6,709,379 B1 * 3/2004 Brandau et al. .................... 600/3
6,729,356 B1 * 5/2004 Baker et al. ............... 139/387 R
7,018,405 B2 * 3/2006 Sirhan et al. ................. 623/1.42
7,384,660 B2 * 6/2008 Hossainy et al. ............ 427/2.25
2002/0004681 A1 * 1/2002 Teoh et al. .................... 623/1.42
2003/0004563 A1 * 1/2003 Jackson et al. ............... 623/1.15
2003/0144727 A1 * 7/2003 Rosenthal et al. ........... 623/1.15
2003/0190406 A1 * 10/2003 Hossainy et al. ............ 427/2.25
2004/0185081 A1 * 9/2004 Verlee et al. .................. 424/423
2004/0236415 A1 * 11/2004 Thomas ........................ 623/1.42
2005/0021127 A1 * 1/2005 Kawula ........................ 623/1.15
2005/0100582 A1 * 5/2005 Stenzel .......................... 424/426
2005/0119723 A1 * 6/2005 Peacock ........................ 623/1.15
2005/0203613 A1 * 9/2005 Arney et al. .................. 623/1.42
2006/0020329 A1 * 1/2006 Raze et al. .................... 623/1.42
2006/0025848 A1 * 2/2006 Weber et al. .................. 623/1.15
2006/0184237 A1 * 8/2006 Weber et al. .................. 623/1.44

* cited by examiner

*Primary Examiner* — David Isabella
*Assistant Examiner* — Jonathan R Stroud
(74) *Attorney, Agent, or Firm* — Brooks, Cameron & Huebsch, PLLC

(57) ABSTRACT

An endovascular graft of the present invention embodies a graft system utilizing the textile fabric of the prosthesis for drug storage and delivery. These drug-eluting devices involve treating the textile fabric with therapeutic agents to provide a method of delivery to both the outer surface of the graft and the inner surface of the graft. An endovascular graft system having a fuzz texturing on the outer periphery of the graft where the texturing includes a therapeutic agent coating applied to the texturing material is also contemplated. An expandable attachment frame further includes drug storage and delivery capabilities in the cavities formed in the V-hooks and apices. Therapeutic agents can also included in the radio-paque coating or loading to serve as a reservoir for controlled drug delivery.

15 Claims, 5 Drawing Sheets

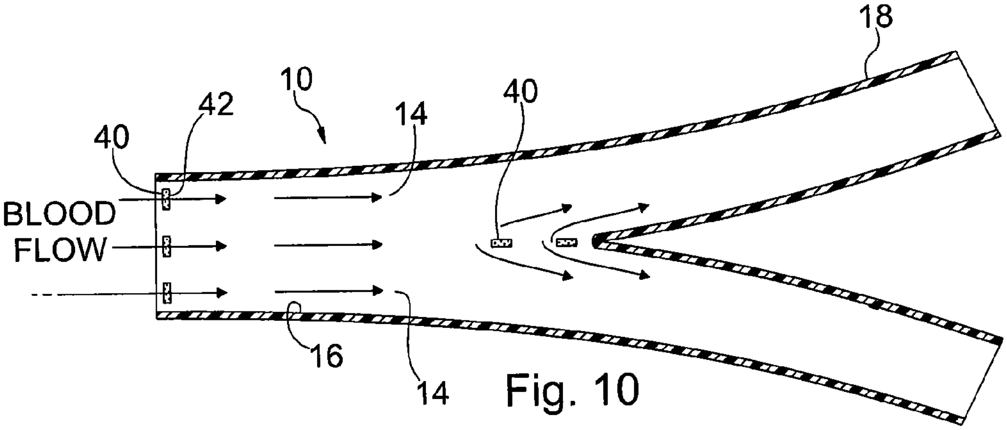
Fig. 10
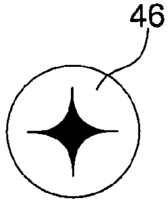
Fig. 11
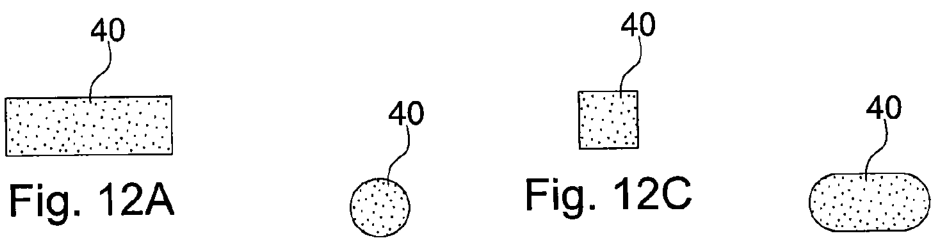
Fig. 12A
Fig. 12B
Fig. 12C
Fig. 12D

DRUG DELIVERY ENDOVASCULAR GRAFT

BACKGROUND OF THE INVENTION

The present invention relates generally to vascular repair devices, and more particularly to intravascular devices which are adapted to be implanted into a patient's body lumen, such as a blood vessel or coronary artery, to maintain the patency and for the delivery of therapeutic agents thereof.

It is well established that various fluid conducting body or corporeal lumens, such as veins and arteries, may deteriorate or suffer trauma so that repair is necessary. For example, various types of aneurysms or other deteriorative diseases may affect the ability of the lumen to conduct fluids and, in turn, may be life threatening. In some cases, the damage to the lumen is repairable only with the use of prosthesis such as an artificial vessel or graft.

For repair of vital lumens such as the aorta, surgical repair is significantly life threatening or subject to significant morbidity. Surgical techniques known in the art involve major surgery in which a graft resembling the natural vessel is spliced into the diseased or obstructed section of the natural vessel. Known procedures include surgically removing the damaged or diseased portion of the vessel and inserting an artificial or donor graft portion inserted and stitched to the ends of the vessel which were created by the removal of the diseased portion. More recently, devices have been developed for treating diseased vasculature through intraluminal repair. Rather than removing the diseased portion of the vasculature, the art has taught bypassing the diseased portion with a prosthesis and implanting the prosthesis within the vasculature. An intra arterial prosthesis of this type has two components: a flexible conduit, the graft, and the expandable framework, the stent (or stents). Such a prosthesis is called an endovascular graft.

It has been found that many abdominal aortic aneurysms extend to the aortic bifurcation. Accordingly, a majority of cases of endovascular aneurysm repair employ a graft having a bifurcated shape with a trunk portion and two limbs, each limb extending into separate branches of vasculature. Currently available bifurcated endovascular grafts fall into two categories. One category of grafts are those in which a preformed graft is inserted whole into the arterial system and manipulated into position about the area to be treated. This is a unibody graft. The other category of endovascular grafts are those in which a graft is assembled in-situ from two or more endovascular graft components. This latter endovascular graft is referred to as a modular endovascular graft.

Intravascular interventional devices such as stents are typically implanted within a vessel in a contracted state, and expanded when in place in the vessel in order to maintain the patency of the vessel to allow fluid flow through the vessel. Stents have a support structure such as a metallic structure to provide the strength required to maintain the patency of the vessel in which it is to be implanted, and are typically provided with an exterior surface coating to provide a biocompatible and/or hemocompatible surface. Since it is often useful to provide localized therapeutic pharmacological treatment of a blood vessel at the location being treated with the stent, it is also desirable to provide intravascular interventional devices, other than stents, with a biocompatible and/or hemocompatible surface coating of a polymeric material with the capability of being loaded with therapeutic agents, to function together with the intravascular devices for placement and release of the therapeutic drugs at a specific intravascular site.

Drug-eluting stent devices have shown great promise in treating coronary artery disease, specifically in terms of reopening and restoring blood flow in arteries stenosed by atherosclerosis. Restenosis rates after using drug-eluting stents during percutaneous intervention are significantly lower compared to bare metal stenting and balloon angioplasty. Restenosis is the normal reaction of the human body to a foreign body being implanted in one of the coronary, carotid, or peripheral arteries. The coating of bare metal stents with an anti-cancer drug is the current approach to decrease or eliminate restenosis. However, current design and fabrication methods for drug-eluting stent devices are not optimal. Accordingly, various limitations exist with respect to such current design and fabrication methods for drug-eluting stents.

One significant limitation, for example, is that current designs for drug-eluting stents fail to provide for uniform drug distribution in the artery. Since uniformity is dictated by metal stent skeletal structure, increasing uniformity by increasing the metal stent surface area makes the stent stiff and compromises flexibility and deliverability. Further limitations include the mixture of the drug in a polymer and/or solvent solution which is then spray coated on the entire stent surface with a primer, drug, and topcoat layers being used to control release kinetics. This approach tends to cause cracking in the drug-coating layer, since the layer also undergoes stretching during stent expansion, and resultant considerable washout of the drug into the blood stream, and only a fraction gets into the tissue/artery. Further, the amount of the drug that can be loaded on the stent is limited by mechanical properties of the coating, since the higher drug content in the polymer makes the coating more brittle and causes cracking thereto. Therefore, loading a higher drug dose requires coating with more polymer on the device. Other limitations in current fabrication methods of drug-eluting stents include the necessity of several coating steps along the length of the stent which is time consuming. As conventional spray coating is capable of programming only one drug release rate kinetics, variation of drug dosing and release kinetics along the length of the stent is not possible using the current coating process.

Several challenges face the major medical device manufacturing companies in regard to implementing a drug-eluting stent into the marketplace. A common method of applying an anti-cancer drug for example, is to first apply a polymer primer layer to the bare metal stent, dissolve the drug into a suitable polymer using a suitable solvent, spray the drug-polymer mixture onto the primer layer, and then apply a polymer topcoat. One particular challenge facing endovascular graft medical device manufacturers is providing a drug elusive device having a flexible graft covering the drug-polymer layered expandable stent. Medical device manufacturing companies are also faced with the challenge of making drug-eluting devices that have adequate drug storage capability. The creation of channels and/or depots into tubing using laser machining is one approach that has been considered to resolve this issue. However, it has been found that laser machining requires more control (i.e., consistency) in order to be a reliable and controlled manufacturing process. For example, in forming depots using laser machining, the depth thereof is not precisely repeatable from one depot to the next. Further, studies have shown that the use of laser machining in creating channels and/or depots into tubing is not a cost effective way to manufacture high volumes of components with intricate geometric shapes and designs at a competitive price.

What has been needed and heretofore unavailable in the art is a method of manufacturing endovascular grafts for the subsequent manufacture into drug-eluting devices that would increase the reservoir capacity of the device by incorporating longitudinal and/or circumferential channels and geometrically-shaped depots into the endovascular graft structure. Thus, it would be desirable to have a drug-eluting device that is optimally designed to have increased drug storage capability, which improves the reproducibility of drug storage features currently being manufactured. The present invention meets these and other needs.

INVENTION SUMMARY

Briefly and in general terms, the present invention is directed to repairing vasculature and preventing restenosis in the treated area. Endovascular grafts are particularly useful in the treatment of atherosclerotic stenosis in arteries and blood vessels. More particularly, the invention concerns apparatus and methods of manufacturing endovascular grafts for the subsequent manufacture into drug-eluting stents. These devices may have longitudinal/circumferential channels and/or depots directly formed into the graft thereof to enable such devices to act as functional drug delivery vehicles having adequate drug reservoir capabilities. Therapeutic agents or drugs are also attached to the graft fabric for controlled drug delivery into the vasculature system.

The endovascular graft of the present invention includes: a graft body having a plurality of openings defining the superior, ipsilateral and contralateral members of a bifurcated graft; an expandable frame capable of intraluminally attaching a superior opening to a vessel; and a means for delivering a therapeutic agent or drug, loaded within the endovascular graft system, to the area to be treated.

The advantages of the present invention are achieved with delivery of the therapeutic agent or drug from the endovascular graft system. In one embodiment, a substantially conventional endovascular graft body is coated or impregnated with a therapeutic agent. The invention utilizes the textile fabric of the graft for storage and delivery of the therapeutic agent. The material for the graft body can be varied and may consist of currently available fabrics. A greige-graft, non processed material that is treated with a polymer coated agent which would release the drug at a specific time is an operable fabric for the present embodiment. The drug coated endovascular graft coating can include anti-inflammatory, anti-clotting agents and anti-hypertensive drugs.

In another embodiment of the present invention, the graft body includes a textured member circumferentially affixed to the graft body. The textured member is defined by a tufted material formed from loose fibers and loaded with the therapeutic agent or drug for delivery therein. Application of the tufted material is such that the tuft is affixed to the outer periphery of the graft where a portion of the filaments extend through the graft material to the inner surface of the graft, thus providing drug delivery means on both surfaces. Materials for the tufted material includes a polyethyleneterephthalate (PET) fabric.

In one aspect of the present embodiment, the tufted material can be a plurality of fibers that are spun, woven, knotted, pressed or otherwise loosely associated to form a textured material. The tufted material can also be formed from a non-woven web of loose fibers circumferentially affixed to the graft superior member. In another aspect, the drug treated tuft is formed from continuous PET suture stitched circumferentially about the graft. The suture providing the drug storage and delivery capabilities for healing the repaired area. In still another aspect of the embodiment, the tufted material is configured in layers to provide a timed delayed drug release.

In a further embodiment, the graft body includes a plurality of enclosures or pillows configured for storage and delivery of a therapeutic agent or drug. The pillows are sewn, or attached by other means, into the graft inner surface. The pillows can be configured in different shapes and sizes that provide for the appropriate level of drug loading and treatment. The material encapsulating the therapeutic agent varies, and may include the same material forming the graft.

In another aspect of the drug loaded pillow embodiment, the therapeutic agent or drug is formed in the shape of a pillow and attached therein the graft fabric. This pillow is designed to dissipate over time.

In yet another embodiment, radiopaque markers are loaded or coated with a therapeutic agent or drug to serve as reservoirs for controlled drug delivery. The radiopaque markers are configured with a slight opening for loading and releasing the therapeutic agent into the vasculature system. The size and shape of the radiopaque markers varies according to the desired level of loading with radiopaque particles and therapeutic agents.

In still another embodiment, an expandable attachment frame comprises a plurality of cavities, the cavities being configured to hold the therapeutic agent therein. The cavities are formed from the V-hooks and apices configured on the graft frame. The therapeutic agent or drug is loaded in the cavities or crevices and released into the vasculature system after graft delivery. Alternatively, a therapeutic agent or drug can be coated on the attachment system frame for drug delivery. At least a portion of the expandable frame can be coated with a primer material, which adheres to the frame, the primer material being coated with at least one layer of the therapeutic agent.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 10 is a side cross-sectional view of an endovascular graft incorporating radiopaque markers having a therapeutic agent packed therein;

FIG. 11 illustrates a drug impacted radiopaque marker having a slight opening for drug release;

FIGS. 12A-D illustrate the various shapes of drug impacted radiopaque markers.

DETAILED DESCRIPTION OF THE PREFERRED EMBODIMENTS

The vascular repair devices of present invention are employed to maintain the patency of selected body lumens and for the delivery of therapeutic agents or drugs. As illustrated in the figures, the advantage afforded the repair device is the ability to provide therapeutic agents which may be configured for controlled drug delivery to the bifurcated treatment area in an abdominal aorta. Repair of vessels that are diseased at a bifurcation is particularly challenging since the stent or graft must be precisely positioned, provide access to any diseased area located distal to the bifurcation, and maintain vessel patency inorder to allow adequate blood flow to reach the myocardium. It is often useful to provide localized therapeutic pharmacological treatment of a blood vessel at the location being treated with the graft.

In general, the endovascular graft of the present invention embodies a graft system utilizing the textile fabric of the prosthesis for drug storage and delivery. Treating the textile fabric with therapeutic drugs provides a method of delivery to both the outer surface of the graft and the inner surface of the graft. Preventing restenosis after endovascular treatment is one example of the advantages of the present invention, that is, drugs such as anti-stenosis agents can be delivered from the textile fabric or other structure of the graft system.

Figure 1:
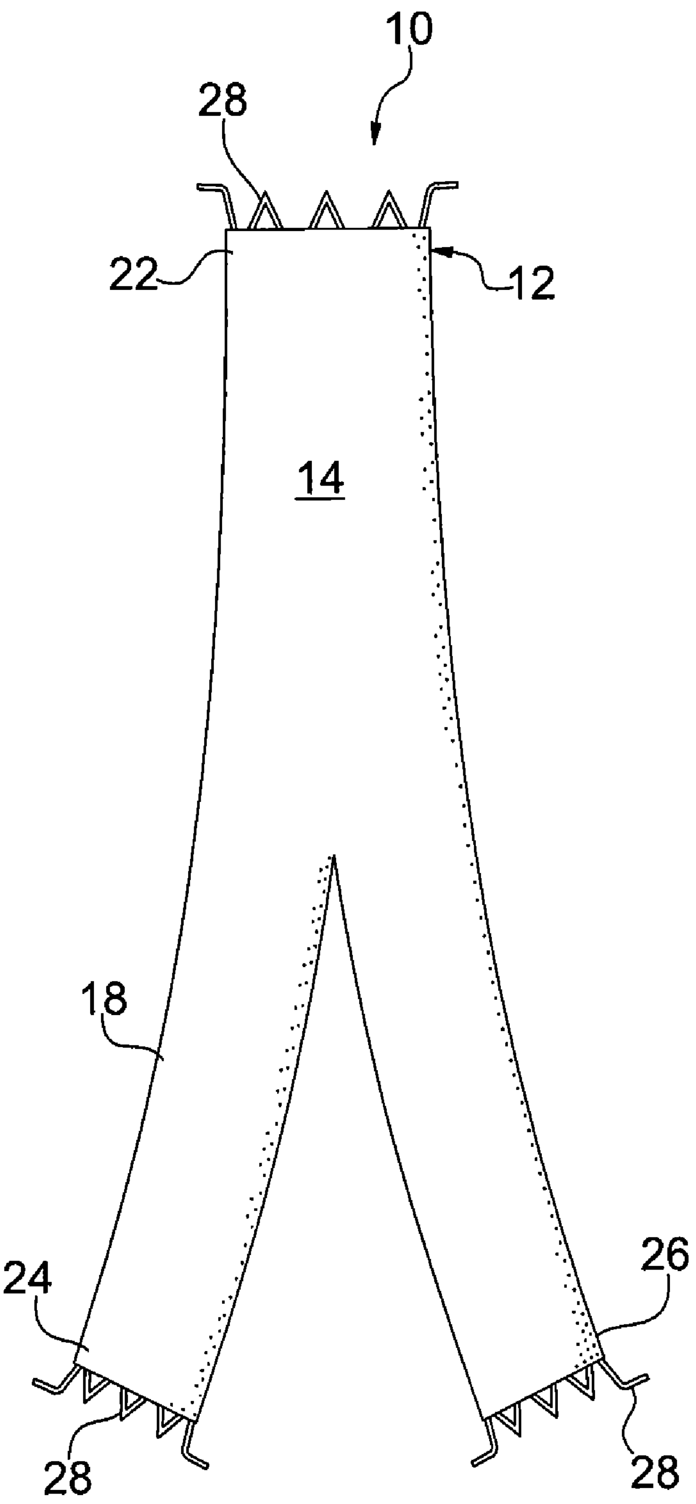
FIG. 1 is an elevational view of an endovascular graft incorporating a therapeutic coating.

FIG. 1 illustrates an endovascular graft configured with a therapeutic agent coating applied to the textile material forming the graft. The drug coated endovascular graft provides similar drug eluting capabilities as a stent. As a drug coated implant after implantation inside the vascular system, the drug coated graft acts as a carrier for certain drug agents, which would be released once inside the vessel wall to be delivered at an interventional site or throughout the patient's body.

In forming a graft for drug coating, the material used can be a non-processed woven or knitted fabric as it leaves the loom or knitting machine, i.e., before any bleaching, dyeing or finishing treatment has been given to them. For some of these graft fabrics, the term greige-graft is used to describe such materials. In the present invention, the greige-graft, non-processed material is first treated with a polymer coated agent which would release at specific times. The polymer coated agents may also be left on the greige-graft for dissipation through PET 2% degradation over time.

A greige-graft application process to coat a graft fabric with a specific drug polymer can be operable when a predetermined incubation oven and bio-chemical adhesives show presence and release of the drug in the body after time. Treatment of the graft includes an application "bath" of the fabric into the drug compounds, then dried and sealed, and further including biocompatibility treatment of all addition materials. Past commercialization use of aluminum coating has been used as an added advantage being the elimination of the need for a pre-clotting agent.

The drug coated endovascular graft coatings may include such drug coatings as anti-inflammatory and anti-clotting agents to assist abdominal aorta aneurysm healing. Suitable drugs for treatment may include any of the biocompatible drugs available in the market.

Certain fabric silver-nitrate filaments have been developed, that when disposed on the exterior tissue surfaces, have acted like anti-microbial agents upon bacterial infections. A drug coated endovascular fabric could act as a polymer drug eluting surface for preventing the spread infection. Recent studies on anti-hypertensive drug association with AAA revealed that patients with calcium-channel antagonists, i.e. Amlodipine, beta-blockers, or ACE inhibitors showed decrease stiffness in the aorta wall, which was exhibited to be proportionate to AAA elastase. Such drugs could be adhered to graft filaments and subsequently released from the fabric at controlled intervals. The use of textile fabrics allows for fabric coatings of materials that will adhere to the fabric, as well as, materials that can be coated and then woven into the fabric.

Figure 2:
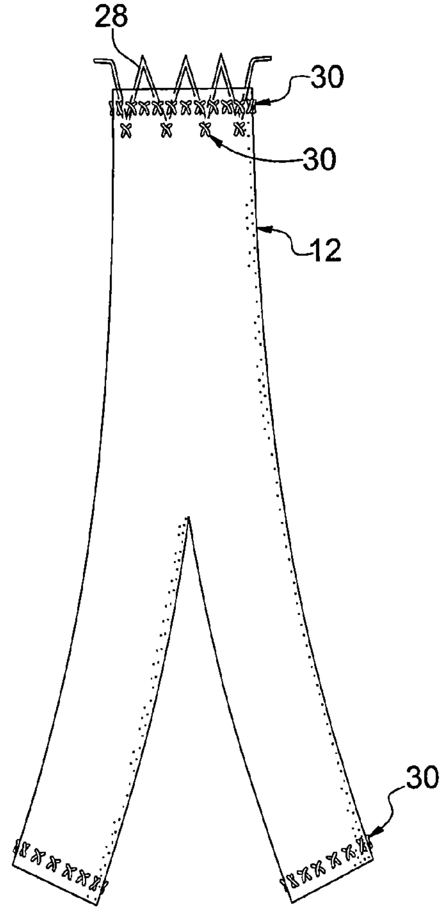
FIG. 2 is an elevational view of an endovascular graft incorporating a tuft coated with a therapeutic agent.
Figure 3:
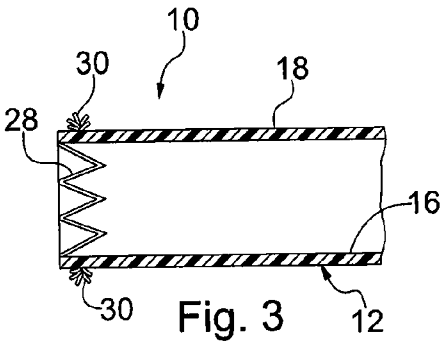
FIG. 3 is a side partial cross-sectional view depicting tuft coated with a therapeutic agent.

FIG. 2 illustrates an endovascular graft of the present invention having a texturing 30 on the outer periphery of the graft where the texturing includes a therapeutic agent coating applied to the texturing material. The texturing on the graft outer periphery 18 can be accomplished with a plurality of filaments or fibers that are spun, woven, knotted, pressed or otherwise loosely associated to form a fuzzed or puffed textured filler that can be treated with a therapeutic agent and sewn to or affixed to the outside of the graft. Preferably, as shown in FIGS. 2, 3, 5 and 6, the fuzz or texturing is configured to radially surround a graft and in the case of a bifurcated graft, about the superior, ipsilateral and contralateral members defining the bifurcated graft.

The fuzzed material may be formed of the same material as the graft, alternatively the fuzzed material may embody tufts 30 including a biocompatible synthetic material. The tufts 30 may be configured from a polyethyleneterephthalate (PET) fabric formed from a non-woven web of loose fibers stitched circumferentially around the graft member site. The tufted material being attached to the graft member walls 20, such that the fabric is exposed on the outside of the graft 18 and a portion exposed on the inside of the graft 16 (See FIG. 3). The drug coated tufted material may also be utilized to attach an expandable frame or attachment system 28 to the graft fabric 12. In one aspect, the attachment frame 28 is secured at the superior member 22 of a bifurcated graft 10 with the drug coated attachment tufts 30, the therapeutic agent being released from the point of attachment.

Figure 4:
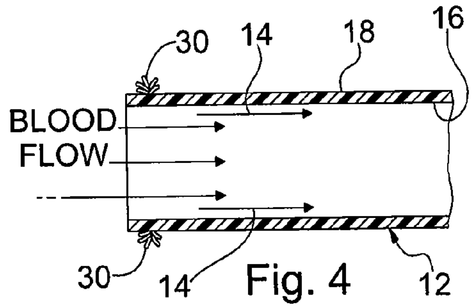
FIG. 4 is a cross-sectional view of the endovascular graft of FIG. 2, depicting the therapeutic agent release and blood flow therein.

FIG. 4 is a cross-sectional view of the graft of the present invention depicting the tuft 30 coated with a therapeutic agent releasing the drug on the inside of the graft 16 and flowing therein into the vascular system for treatment of the affected area. A continuous blood flow over the tufted material at or near the attachment site, i.e. attachment of the tuft 30 to the graft and attachment of the attachment frame 28 to the graft 10, causes the drug treated fabric to be released.

Figure 5:
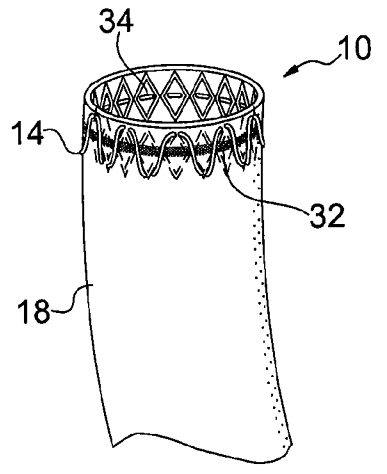
FIG. 5 is a side elevational view of an endovascular graft wherein the tufted web is depicted.

In another embodiment of the present invention, a drug coated tufted layer of PET fabric 32 made from a non-woven web of loose fibers is simply attached to the outer wall 18 of the graft 10 by stitching the fiber on to the wall of the of the tubular member 20 (See FIG. 5). Magnification of the non-woven PET fabric reveals loose openings between fibers, similar to a velour graft, but porous enough to allow blood flow through and around the layered material. The non-woven PET web 32 has an in air thickness of approximately 0.01 in., the compressed thickness is approximately 0.007-0.008 in., and the width of the fabric is approximately 5 cm wide. The drug treatment of the tufted material can be by coating or impregnation.

Figure 6:
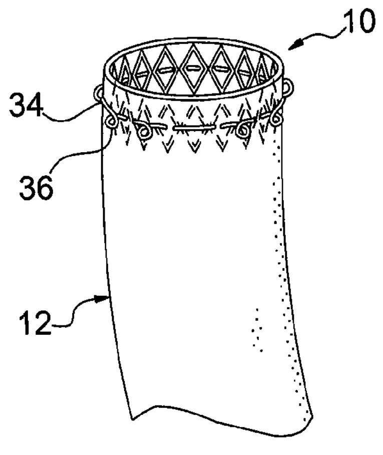
FIG. 6 is a side elevational view of an endovascular graft, wherein the tufted loop is depicted.

As shown in FIG. 6, a drug treated tuft is formed of continuous PET suture 34 stitched circumferentially about a graft 10. The suture stitching pattern would alternate in-and-out of the attachment system frame 28 forming a small 2-2.5 mm loop staggered evenly around the attachment site. The PET loops 36 of the tuft provide a surface which can be coated with a therapeutic agent or impregnated with such agent for timed release within the vascular system.

Figure 7:
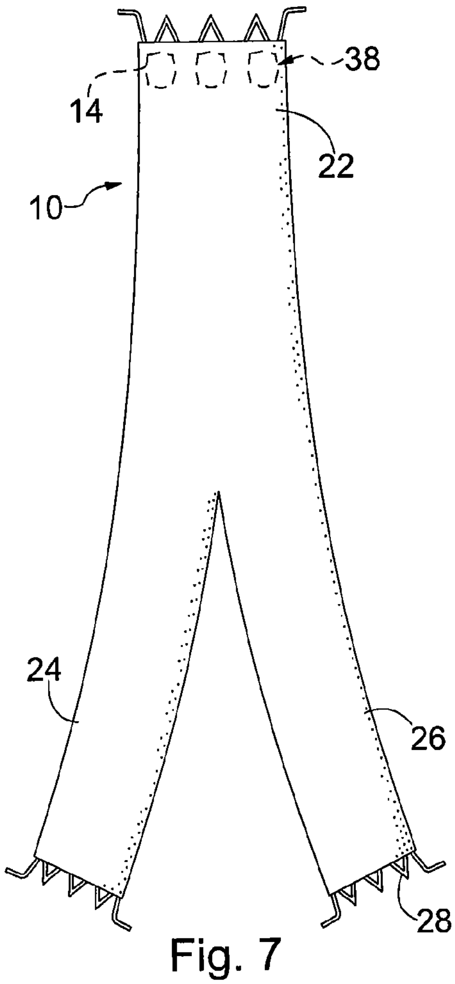
FIG. 7 is an elevational view of an endovascular graft incorporating therapeutic pillows sewn on the inside surface.
Figure 8:
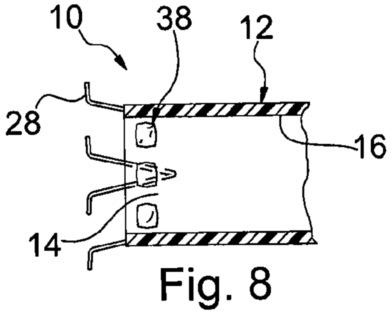
FIG. 8 is a side partial cross-sectional view of the endovascular graft of FIG. 7.
Figure 9:
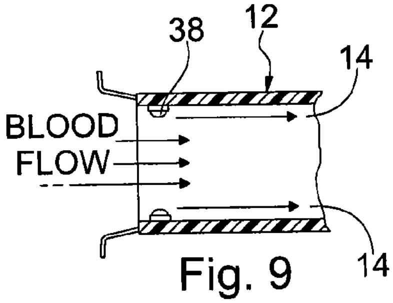
FIG. 9 is a cross-sectional view of the endovascular graft illustrating the therapeutic agent release and flow.

FIGS. 7-9 illustrates an endovascular graft having enclosures 38 sewn into the graft fabric 12, the enclosures or pillows 38 being loaded with a therapeutic agent or drug 14 for delivery at an interventional site. A plurality of drug loaded pillows 38 are attached circumferentially around the superior member 22 inner side 16 (See FIGS. 7-8). The drug filled enclosures can be formed in different shapes and sizes which project inwardly into the blood flow. Suitable materials for the drug filled enclosures includes fabrics which allow absorption of blood there through, thus inducing the drug delivery. As shown in FIG. 9, the drug or therapeutic agent 14 is released on the graft inner surface 16, the drug 14 then being released into the blood flow within the treated area.

In another aspect of the invention, the therapeutic agent itself may be configured in the form of a pillow and attached to the inner side of the graft system, allowing the agent direct contact with the blood flow through the graft and rapid drug delivery. In still another aspect of the present invention, the pillows can be layered to provide for drug release in stages.

It is well known in the art that the physical attachment of radiopaque markers to stents and endovascular grafts accomplishes fluoroscopic visibility. As illustrated in FIG. 10, therapeutic agents may be encapsulated or included in the coating of a radiopaque marker 40 to serve as a reservoir for controlled drug delivery. The advantages of the present invention also can be achieved with the complete encapsulation of radiopaque particles and therapeutic agents within a binder or coating 42 that is dispersed onto the inside or other surface 16 of the graft fabric 12. Radiopaque particles are then placed in a binder which has satisfactory bio- and hemo-compatibility. The binder 42 can be coated on all surfaces of the graft in such a manner to produce a smooth surface. The thickness and particle loading of the radiopaque material and therapeutic agent can be adjusted to fine tune the degree of radiopacity needed, depending upon the choice of material used to create the stent. The radiopaque coating/binder 42 may be applied by spraying, dipping, brushing, wiping, pad printing, electrostatic liquid spraying or electrostatic powder coating. A radiopaque coating/binder 42 thickness should be in the range of about 0.1 to 25 microns, preferably in the range of 1 to 10 microns. Large coating thicknesses may possibly alter the geometry of the graft. Materials for the binder can be varied and may consist of synthetic polymers or biopolymers.

As shown in FIG. 11, the radiopaque markers 40 are configured with a slight opening 46 wherein the therapeutic agent or drug is packed and from which the therapeutic agent is released during delivery. FIGS. 12A-D illustrate various shapes, e.g. rectangular, circular, square, and oval, that the radiopaque marker 40 may be formed. These shapes are meant for illustration purposes and should not be considered limiting in any manner. The radiopaque markers 40 can be sewn, clipped or glued onto the inside 16 of the graft material 12. Existing products can adopt this embodiment of the present invention by moving it's radiopaque markers from the outer surface of the graft to the inner side. The drug packed radiopaque marker also can be coil shaped.

In another aspect of the present embodiment of the invention, the drug packed radiopaque markers 40 can be configured to activate drug delivery when an alloy stent or graft attachment frame 28 is delivered and/or deployed over the marker. In still another aspect of the present embodiment, the drug packed radiopaque markers 40 can be attached to a superior, ipsilateral or contralateral member of a modular endovascular graft that is delivered later into the graft system 10, thus extending drug treatment.

Figure 13:
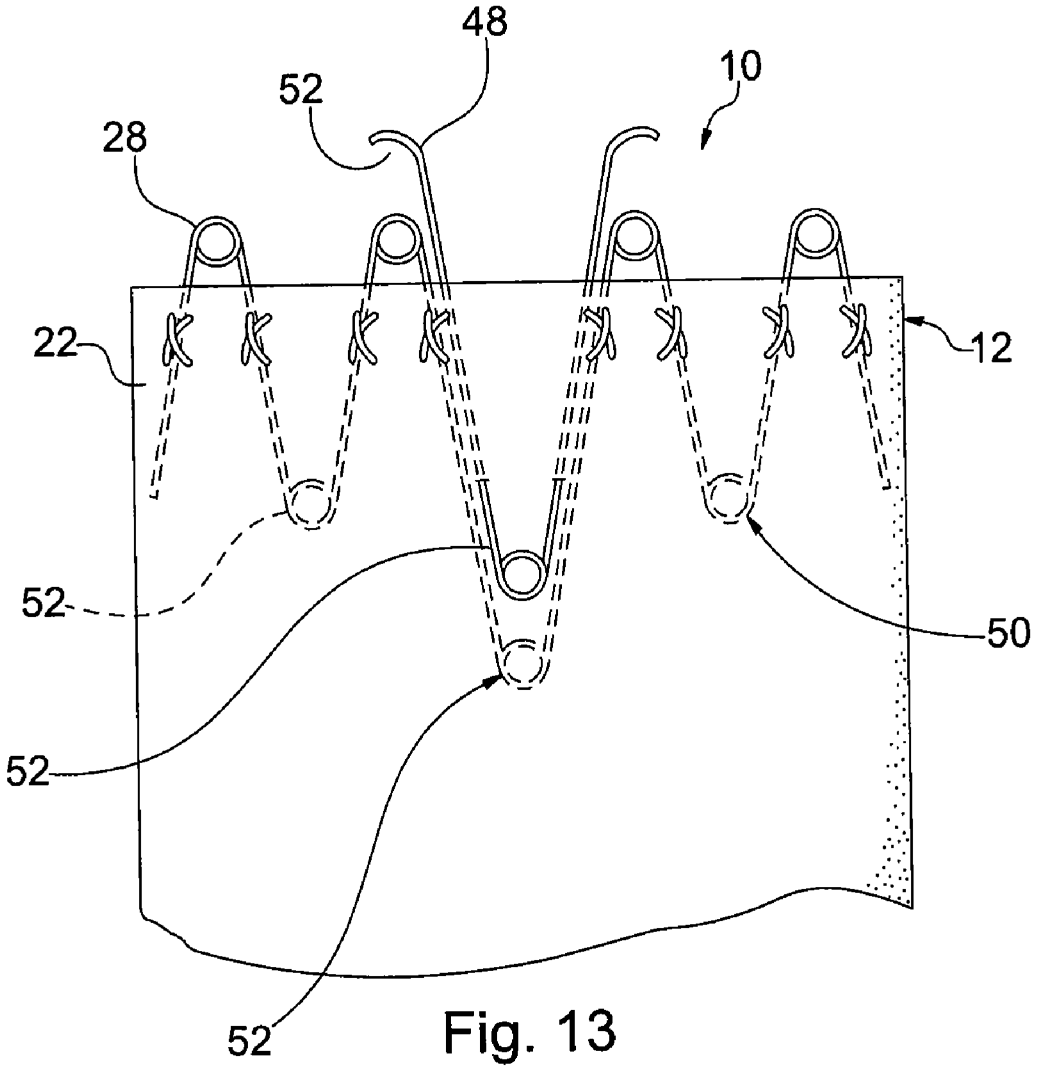
FIG. 13 is an elevational view of a portion of the endovascular graft system having therapeutic agents packed within the attachment frame cavities formed from the V-hooks and apices.

The endovascular graft 10 attachment system 28 of the invention also can be coated with a drug or therapeutic agent to assist in repair of a vessel and may be useful, for example, in reducing the likelihood of the development of restenosis. As illustrated in FIG. 13, the V-hooks 48 and apices 50 of the frame 28 may be coated with the therapeutic agent configured for drug delivery. Preferably, the therapeutic agent is packed into cavities or crevices 52 on the frame which can hold the drug. The drug delivery invention can be used for any type of graft frames having a cavity opening 52 that can hold a drug. This invention is adaptable to existing alloy frames on the market, since there is no requirement for additional parts to be added to the graft system for drug delivery treatment capabilities. Another aspect of this invention is that the therapeutic agent can be configured for placement within the circular apice 50 opening on the attachment frame 28.

Further, it is well known that the graft attachment frame 28 (usually made from a metal) may require a primer material coating to provide a substrate on which a drug or therapeutic agent is coated since some drugs and therapeutic agents do not readily adhere to a metallic surface. The drug or therapeutic agent can be combined with a coating or other medium used for controlled release rates of the drug or therapeutic agent.

Examples of therapeutic agents or drugs that are suitable for use in accordance with the present invention include 17-beta estradiol, sirolimus, everolimus, actinomycin D (ActD), taxol, paclitaxel, or derivatives and analogs thereof. Examples of agents include other antiproliferative substances as well as antineoplastic, antiinflammatory, antiplatelet, anticoagulant, antifibrin, antithrombin, antimitotic, antibiotic, and antioxidant substances. Examples of antineoplastics include taxol (paclitaxel and docetaxel). Further examples of therapeutic drugs or agents include antiplatelets, anticoagulants, antifibrins, anti-inflammatories, antithrombins, and antiproliferatives. Examples of antiplatelets, anticoagulants, antifibrins, and antithrombins include, but are not limited to, sodium heparin, low molecular weight heparin, hirudin, argatroban, forskolin, vapiprost, prostacyclin and prostacyclin analogs, dextran, D phe pro arg chloromethylketone (synthetic antithrombin), dipyridamole, glycoprotein IIb/IIIa platelet membrane receptor antagonist, recombinant hirudin, thrombin inhibitor (available from Biogen located in Cambridge, Mass.), and 7E 3B® (an antiplatelet drug from Centocor located in Malvern, Pa.). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen located in the United Kingdom), angiotensin converting enzyme inhibitors such as Captopril® (available from Squibb located in New York, N.Y.), Cilazapril® (available from Hoffman LaRoche located in Basel, Switzerland), or Lisinopril® (available from Merck located in Whitehouse Station, N.J.); calcium channel blockers (such as Nifedipine), colchicine, fibroblast growth factor (FGF) antagonists, fish oil (omega 3 fatty acid), histamine antagonists, Lovastatin® (an inhibitor of HMG CoA reductase, a cholesterol lowering drug from Merck), methotrexate, monoclonal antibodies (such as PDGF receptors), nitroprusside, phosphodiesterase inhibitors, prostaglandin inhibitor (available from GlaxoSmithKline located in United Kingdom), Seramin (a PDGF antagonist), serotonin blockers, steroids, thioprotease inhibitors, triazolopyrimidine (a PDGF antagonist), and nitric oxide. Other therapeutic drugs or agents which may be appropriate include alpha-interferon, genetically engineered epithelial cells, and dexamethasone.

While the foregoing therapeutic agents have been used to prevent or treat restenosis, they are provided by way of example and are not meant to be limiting, since other therapeutic drugs may be developed which are equally applicable for use with the present invention. The treatment of diseases using the above therapeutic agents is known in the art. The calculation of dosages, dosage rates and appropriate duration of treatment are previously known in the art. Furthermore, the therapeutic drugs or agents are loaded at desired concentration levels per methods well known in the art to render the device ready for implantation.

It should be understood that any reference in the specification or claims to a drug or therapeutic agent being coated on the endovascular graft system is meant that one or more layers can be coated either directly on the graft or onto a primer material on the graft attachment system to which the drug or therapeutic agent readily attaches.

While particular forms of the invention have been illustrated and described, it will be apparent to those skilled in the art that various modifications can be made without departing from the scope of the invention. Accordingly, it is not intended that the invention be limited except as by the appended claims.

While the specification describes particular embodiments of the present invention, those of ordinary skill can devise variations of the present invention without departing from the inventive concept.

We claim:

1. An endovascular graft system, comprising:

a graft body;

a frame; and a therapeutic agent loaded within the endovascular graft system for release of the therapeutic agent therein, wherein a secondary structure retains the therapeutic agent relative to the graft body, the secondary structure comprising a tufted material attached to a wall of the graft body such that at least a portion of the tufted material extends through the graft body to expose tufts inside a lumen for flow of blood of the graft body and at least a portion of the tufted material has tufts exposed outside of the graft body as a therapeutic agent reservoir, the portion of the tufted material exposed inside the lumen of the graft body configured to release the therapeutic agent from the reservoir through the tufts into the lumen of the graft body as the blood flows therethrough;

wherein the tufted material is configured to radially surround the graft only at a superior or an inferior end, and in a bifurcated graft only to radially surround one or more ends of superior, ipsilateral, and contralateral members defining the bifurcated graft; and wherein the therapeutic agent is an anti-stenosis drug to maintain patency of the lumen of the endovascular graft system.

2. The system of claim 1, wherein the graft body is bifurcated defining a superior member, an ipsilateral member and a contralateral member.

3. The system of claim 1, wherein the secondary structure is coated with the therapeutic agent.

4. A system for treating a body lumen, comprising:

a graft body;

a therapeutic agent loaded within the system for release of the therapeutic agent therein, wherein a secondary structure retains the therapeutic agent relative to the graft body, the secondary structure comprising a tufted material attached to a wall of the graft body such that at least a portion of the tufted material extends through the graft body to expose tufts inside a lumen for flow of blood of the graft body and at least a portion of the tufted material has tufts exposed outside of the graft body as a therapeutic agent reservoir, the portion of the tufted material exposed inside the lumen of the graft body configured to release the therapeutic agent from the reservoir through the tufts into the lumen of the graft body as the blood flows therethrough;

wherein the tufted material is configured to radially surround the graft only at a superior or an inferior end, and in a bifurcated graft only to radially surround one or more ends of superior, ipsilateral, and contralateral members defining the bifurcated graft; and wherein the therapeutic agent is an anti-stenosis drug to maintain patency of the lumen of the endovascular graft system.

5. The system of claim 4, wherein the secondary structure is coated with the therapeutic agent.

6. The system of claim 4, wherein the secondary structure is impregnated with the therapeutic agent.

7. The system of claim 4, wherein the secondary structure is circumferentially affixed to an outer periphery adjacent an open end of at least one of a graft body superior member, an ipsilateral member, and a contralateral member of the graft body.

8. The system of claim 7, wherein the tufted material is a plurality of fibers that are spun, woven, knotted, pressed or otherwise loosely associated to form a textured material.

9. The system of claim 7, wherein the tufted material is formed from a non-woven web of loose fibers.

10. The system of claim 7, wherein the tufted material is configured from a polyethyleneterephthalate.

11. The system of claim 7, wherein the textured member is formed from a suture, the suture being stitched circumferentially around the graft member.

12. The system of claim 7, wherein the tufted material is configured to provide a delayed drug release.

13. The system of claim 4, wherein an attachment system is affixed to the graft body with a suture, the suture being treated with the therapeutic agent.

14. An endovascular graft for repairing a blood vessel, comprising:

a graft body having a plurality of openings;

an expandable frame capable of intraluminally attaching a superior opening to a vessel; and a therapeutic agent loaded within the endovascular graft system for release of the therapeutic agent therein, wherein a secondary structure retains the therapeutic agent relative to the graft body, the secondary structure comprising a tufted material attached to a wall of the graft body such that at least a portion of the tufted material extends through the graft body to expose tufts inside a lumen for flow of blood of the graft body and at least a portion of the tufted material has tufts exposed outside of the graft body as a therapeutic agent reservoir, the portion of the tufted material exposed inside the lumen of the graft body configured to release the therapeutic agent from the reservoir through the tufts into the lumen of the graft body as the blood flows therethrough;

wherein the tufted material is configured to radially surround the graft only at a superior or an inferior end, and in a bifurcated graft only to radially surround one or more ends of superior, ipsilateral, and contralateral members defining the bifurcated graft; and wherein the therapeutic agent is an anti-stenosis drug to maintain patency of the lumen of the endovascular graft system.

15. The graft of claim of 14, the secondary structure circumferentially affixed to the graft body, the tufted material formed from loose fibers loaded with the therapeutic agent.

* * * * *